United States Patent [19]

Ash et al.

[11] 4,448,765
[45] May 15, 1984

[54] LIPOSOMES AND THEIR USE IN TREATING HUMAN OR OTHER MAMMALIAN PATIENTS

[75] Inventors: Philip S. Ash, Colchester; Robert C. Hider, St. Osyth, both of England

[73] Assignee: National Research Development Corporation, London, England

[21] Appl. No.: 54,649

[22] Filed: Jul. 3, 1979

[30] Foreign Application Priority Data

Jul. 3, 1978 [GB] United Kingdom ............... 28612/78

[51] Int. Cl.$^3$ ........................ A01N 25/28; A61J 3/07; A61K 9/58; B32B 9/02
[52] U.S. Cl. ..................................... 424/14; 264/4.7; 424/1.1; 424/16; 424/19; 424/33; 424/38; 424/88; 424/89; 424/94; 424/178; 424/199; 424/238; 428/402.22; 436/829
[58] Field of Search ................... 252/316; 424/19, 36, 424/33, 38, 14; 428/402.22; 436/829

[56] References Cited

U.S. PATENT DOCUMENTS

| | | | |
|---|---|---|---|
| 3,082,154 | 3/1963 | Allan | 424/38 |
| 4,016,100 | 4/1977 | Suzuki et al. | 252/316 |
| 4,089,801 | 5/1978 | Schneider | 252/316 |

FOREIGN PATENT DOCUMENTS

| | | | |
|---|---|---|---|
| 2643641 | 4/1977 | Fed. Rep. of Germany | 424/19 |
| 1211532 | 11/1970 | United Kingdom | 424/168 |
| 1214975 | 12/1970 | United Kingdom | 424/168 |
| 1324745 | 7/1973 | United Kingdom | 424/59 |
| 1539625 | 1/1979 | United Kingdom | 252/316 |
| 2008433 | 6/1979 | United Kingdom | 252/316 |

OTHER PUBLICATIONS

Gregoriadis, "The Carrier Potential of Liposomes...", The New England Journal of Medicine, vol. 295, No. 13, (1976), pp. 704-710.
Shieh et al., "Photo-Induced Potentials Across a Polymer Stabilized Planar Membrane...", Biochemical and Biophysical Research Communications, vol. 71, No. 2, (1976), pp. 603-609.
Ash et al., "The Effect of Synthetic Polymers on the Electrical and Permeability Properties . . . ", Biochimica et Biophysica Acta, 510(1978), 216-229.

*Primary Examiner*—Richard D. Lovering
*Attorney, Agent, or Firm*—Oblon, Fisher, Spivak, McClelland & Maier

[57] ABSTRACT

Microvesicles are stabilized by the incorporation of a polymer having aliphatic lipophilic groups with a chain of at least six atoms attached to the backbone thereof. Such microvesicles may incorporate a physiologically active substance such as an antigenic material, an anti-inflammatory agent, a hormone, etc.

20 Claims, No Drawings

LIPOSOMES AND THEIR USE IN TREATING HUMAN OR OTHER MAMMALIAN PATIENTS

This invention relates to liposomes and like materials (microvesicles).

In recent years there has been an increasing interest in the use of liposomes and like materials, particularly as carriers of drugs, and also in other pharmaceutical contexts, for example as immunological adjuvants. Liposomes are widely described in the literature and their general structure is well known; they are onion-like structures comprising a series of lipid layers spaced from one another by aqueous material, with the outermost layer being lipid. Unilamellar bodies comprising a single lipid bilayer enclosing an aqueous compartment have properties related to those of the liposomes and are included therewith by the term microvesicles.

Development of the use of microvesicles has, however, been retarded by the tendency which they show to aggregate on standing into larger microvesicles which ultimately precipitate from solution. It is an object of the present invention, therefore, to provide a method of stabilising microvesicles.

Accordingly the present invention comprises microvesicles which incorporate a polymer having aliphatic lipophilic groups with a chain of at least six atoms attached to the backbone thereof.

It has been found that the incorporation by microvesicles of such a polymer as described above can have a very marked effect upon their stability, for example increasing their half life on storage by fivefold or even more.

Polymers of use in stabilising liposomes may be based upon a wide variety of polymer types since the nature of the polymer backbone is not of primary importance in determining the stabilising effect of the polymer, this effect being due rather to the presence in the polymer of lipophilic groups of the type indicated. Types of polymer which may be used include those having an organic backbone, for example polyvinyl alcohol derived polymers, polyacrylic and polymethacrylic acid derived polymers, and other polyvinyl, polyisobutylene and polyisoprene polymers, all of which contain a backbone consisting of carbon atoms, as well as polymers containing a backbone which includes hetero atoms such as oxygen or nitrogen together with the carbon atoms. Also of some interest are polymers having an inorganic backbone, for example the polyphosphazene polymers. The polymers may be copolymers derived from two or more different type of monomer; in which case it is not usually necessary for the parts of the backbone derived from each of the monomers to carry a lipophilic group, although this may be the case if desired. However, it is generally preferred, that the lipophilic groups make up a significant part, for example 50 or 60% or more, of the molecular weight of the polymer and conveniently also that when both hydrophilic and lipophilic groups are attached to the polymer backbone then the latter predominate.

The lipophilic group will usually comprise a chain of carbon atoms which may be interspersed with heteroatoms such as nitrogen or oxygen and which may either carry only hydrogen atoms or alternatively various substituents. The lipophilic group usually further comprises the residue of some form of functional grouping through which it is attached to the polymer backbone. Various forms of attachment may be used, preferred forms varying according to the basic type of polymer, but a particularly convenient form of residue of use in such attachment is an oxycarbonyl group

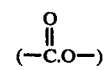

with either the oxygen residue or the carbonyl group being attached to the polymer backbone. In the case of polyvinyl alcohol derived polymers, these are most often of the ester type, the lipophilic group conveniently comprising an ester grouping which has the oxygen residue attached to the polymer backbone. In the case of the polyacrylic and polymethacrylic acid derived polymers, the lipophilic group conveniently comprises an ester grouping which has the carbonyl group attached to the polymer backbone. It will be appreciated that this does not imply that the lipophilic group will necessarily be added to the preformed polymer backbone, for example by means of the formation of an ester linkage. Thus, the polymers used in the compositions of the present invention may be prepared according to various standard procedures described in the art of polymer chemistry and these will most usually involve the polymerisation of a monomer which already contains the lipophilic group. Indeed, it may even be of value to incorporate the monomer into microvesicles and effect polymerisation in situ, for example with UV irradiation.

It has been found that the level of the microvesicle stabilising effect achieved may be considerably enhanced by selection of a lipophilic group of appropriate nature and size. An appropriate selection may, however, depend on a variety of factors including the nature of the lipid used in forming the microvesicles. In general, it is found that the smaller lipophilic groups do not confer stability so readily and larger amounts of polymer are therefore required as compared with somewhat larger groups. However, if the biocompatibility of the polymer should be of particular importance then it may be advantageous to use a larger amount of polymer containing a lipophilic group of smaller size as discussed hereinafter. Most usually, it is preferred to use a lipophilic group with a chain of at least 8 atoms, preferably of at least 10, 12, 13 or 14 atoms, and groups with a chain of 15, 16, 17, 18 and 19 atoms are of particular interest, although larger chains, for example of 20 or 21 atoms up to 24, 25, 26 or 27 atoms may be used. Indeed, the use of even larger chains than this may be considered but it is generally found that polymers containing lipophilic groups with a chain of more than about 29 or 30 atoms present significant problems in use due to their lack of solubility.

As indicated above, the lipophilic group will often consist of a chain of carbon atoms and a functional residue linking group through which it is attached to the polymer backbone. This chain of carbon atoms may be branched and/or saturated (the size of a branched chain being the longest sequence of atoms therein) but is preferably linear, being unbranched and also free from cycloaliphatic rings, and is conveniently also saturated, a particular choice being a residue of a straight chain hydrocarbon. Such a straight chain hydrocarbon residue is often combined with a linking group having a two atom chain, for example an oxycarbonyl group, so that the hydrocarbon residues used will often have a chain length of two atoms less than the whole lipophilic group. Thus, hydrocarbon residues containing chains of 13 to 19 atoms, especially 13 to 17 atoms, such as n-tridecyl, n-tetradecyl, n-pentadecyl, n-hexadecyl, n-heptadecyl, n-octadecyl, oleyl, and n-nonadecyl, are of particular interest.

Reference has been made above to the influence of factors such as the nature of the lipid used to form the microvesicles in the selection of a suitable lipophilic group. Correspondence in size between the chains of the lipid molecule used in the preparation of the microvesicles and those of the lipophilic group can be of some relevance, the sizes of lipophilic group indicated above as being preferred corresponding broadly to the sizes of the chains of the lipids commonly used. In the event that other, larger or smaller, lipids are used in forming the microvesicles, alternative sizes of lipophilic group may be preferred with a chain corresponding more closely in size, for example, within plus or minus two atoms, of that of the lipid.

Examples of specific polymers which may be used in microvesicles according to the present invention are n-tetradecyl polyacrylate and polymethacrylate, n-hexadecyl polyacrylate and polymethacrylate, n-octadecyl polyacrylate and polymethacrylate, and, particularly, polyvinyl myristate, polyvinyl palmitate, and polyvinyl stearate.

The amount of polymer incorporated in order to provide a stabilising effect may be selected over quite a wide range. Although stabilisation may be achieved using high proportions of 1 part by weight of polymer to ten or even as low as four parts by weight of the lipid used in the preparation of the liposomes, the use of smaller proportions of polymer than this is to be generally preferred since the use of the larger proportions may adversely affect the permeability of the microvesicle and may even lead to lower levels of stability than are imparted by the use of smaller proportions. Proportions are therefore conveniently selected at as low a level which is effective in the range from 1 part by weight of the polymer to 20, 50 or particularly 100 parts by weight of lipid down to 1 part by weight of polymer to 200, 300, 400 or particularly 500 parts by weight of lipid. In some cases even less polymer may be used, for example 1 part by weight of polymer to 1,000 parts by weight of lipid, although it will be appreciated that at some stage the level of stabilisation will fall off. However, using a polyvinyl stearate polymer of molecular weight about 7000 good levels of stabilisation have been achieved with 1 part by weight of polymer to 100 parts by weight of lipid, with even better levels at 1:150 and still appreciable stabilisation at 1:500. The above ranges of figures are related most particularly to studies with the polyvinyl stearate polymer system (molecular weight 7,000) and egg yolk lecithin and in the event that a polymer and/or lecithin of significantly different molecular weight are used some variation in proportion may be required to give the best system, although the general indications given above will hold good. Thus, for a polyvinyl laurate polymer/egg lecithin system a ratio of 1 part by weight of polymer to 20 parts by weight of lipid is required to give similar levels of stability as given by the 1:100 ratio for the polyvinyl stearate system described above whilst such a 1:20 ratio is undesirably high for this polyvinyl stearate system.

The ratio of 1:100 weight/weight for polymer:lipid in the polyvinyl stearate (m.w. 7,000)/egg lecithin described above, in which the polymer has a backbone fully substituted by lipophilic groups, corresponds to a molar ratio of about 1:30 for lipophilic group:lipid and a similar factor may be applied if desired to the other ratios given above to produce ranges in molar rather than weight terms.

The efficiency of the polymer in effecting stabilisation may also be influenced by its molecular weight. In general, both very high and very low molecular weights are best avoided. Thus an upper limit of 30,000, 40,000 or 50,000 and a lower limit of 2,000, 3,000, 4,000 or 5,000 is generally selected. Polymers of molecular weight in the range of 5,000 to 30,000, particularly 5,000 to 15,000 and especially 5,000 to 10,000, for example 7,000, are of value in many circumstances. (All references to molecular weight made herein refer to number average molecular weight.)

Microvesicles have a variety of uses. Thus, for example, they provide very suitable models for biological membranes and as such are of value in various biochemical studies. In such a context the microvesicles may not contact any active substance. Microvesicles are, however, generally of most interest when present in a composition which additionally contains some active substance and, as indicated above, compositions containing a biologically active substance are of especial interest. A particularly preferred area is that of pharmaceutical compositions comprising microvesicles which incorporate a physiologically active substance. Such compositions may contain a wide variety of active ingredients, for example drugs including hormones, enzymes, antigenic materials, etc., as exemplified by those compositions described in German OLS Numbers 2249552, 2528411, 2643641, 2712030 and 2712031. Very satisfactory results have been obtained with microvesicles containing such varied active substances as influenza virus antigenic materials, insulin and anti-inflammatory agents, particularly steroids. Indeed, apart from their stabilising effect, the polymers have little effect on the physiological activity of these compositions confirming the wide applicability of the present invention. The liposomes or unilamellar microvesicles may be formed by established procedures which are described in the art comprising the admixture of a lipid in suitable form, for example as a thin film, with an aqueous medium and, where appropriate, involving sonication. It is more common for the active ingredient to be incorporated in the aqueous medium, and in most cases, although not without exception (see German OLS No. 2643641 in respect of virosomes microvesicles incorporating viral antigenic material), the active ingredient is incorporated prior to liposome formation. The polymer may conveniently be incorporated in the lipid prior to microvesicle formation, such a procedure being a suitable method for distributing the polymer through the microvesicle. Although it is believed that the polymer will most usually be substantially contained within the microvesicle, it will be appreciated that there is no reason why this need necessarily apply to the active ingredient which the microvesicles incorporate and this may extend, at least in part, beyond the outer surface of the microvesicle or even be attached to the surface thereof as described, for example, in German OLS No. 2643641.

The lipids employed in the preparation of the liposomes may be varied with respect to such parameters as net charge, degree of branching and length of lipophilic chains. In general, however, the lipid will be selected from those lipids described in the literature for use in the preparation of microvesicles or from variants of such lipids. Preferred lipids are non-immunogenic and biodegradable, and phospholipids such as the lecithins, both natural and synthetic, are often used for the preparation of microvesicle compositions. Examples of such are ovo- or egg yolk-phosphatidyl choline or -lecithin which consists substantially of lipids containing $C_{16}$ to $C_{18}$ hydrocarbon residues with about half of these residues containing one double bond, and the synthetic lecithins di-(tetradecanoyl)phosphatidylcholine,
di-(hexadecanoyl)phosphatidylcholine,
di-(octadecanoyl)phosphatidylcholine,
di-(oleyl)phosphatidylcholine and
di(linoleyl)phosphatidylcholine.

An important consideration in selecting a lecithin or lecithin mixture for the preparation of microvesicles is its phase transition temperature. Preferably this is less than physiological temperature and conveniently also is less than the temperature of preparation of the microvesicles. For this reason the lower phase transition temperatures of natural egg lecithin and synthetic di(-tetradecanoyl) phosphatidylcholine make these lecithins of special interest.

In addition, the microvesicles may also contain other components, for example a material which provides a negative surface charge and in particular various negatively charged acidic compounds containing lipophilic chains including phosphatidic acid, dicetyl phosphate, phosphatidyl serine and the more complex substance beef brain ganglioside. Phosphatidic acid is of particular interest in this respect and may conveniently be isolated from egg yolk lecithin to maintain conformity of the lipid side chains present in the substance used to produce the negative charge and the lipid used to produce the microvesicles. It is also possible to impart a positive surface charge to the microvesicles, for example by the use of stearylamine, although the use of neutral and negatively charged microvesicles is of greater current interest in the context of pharmaceutical compositions.

When the microvesicles are used in a pharmaceutical composition, the polymer is selected with particular regard to its biocompatibility or physiological acceptability. Thus, the polymer is advantageously substantially biodegradable but, alternatively, the polymer may advantageously be substantially biologically inert and be of sufficient low molecular weight, possibly for partial degradation thereof as in the case of the hydrolysis of polyvinyl stearate to polyvinyl alcohol and stearic acid, to be excreted through the kidneys. In this respect, the use of polymers in which a significant part comprises the lipophilic groups is of advantage in giving a low molecular weight polymer after cleavage of these groups.

Biodegradability and elimination of the polymer from the system may conveniently also be aided by the selection of polymers which are essentially hydrophilic in nature as regards the backbone of the polymer and any functional groups, the residues of which are used for attachment of the remainder of the lipophilic group to the polymer backbone. In this way the whole polymer, which is essentially hydrophobic, will become essentially hydrophilic upon cleavage of the lipophilic groups at the functional group residue with regeneration of this group on the polymer backbone.

The invention is illustrated by the following Examples.

EXAMPLE 1

Preparation of microvesicles

Ovo-lecithin prepared by the method of Dawson, Biochemical Journal 1963, 88, 414 (150 mg) is dissolved in chloroform (1.0 ml) and to the solution is added polyvinyl stearate (1 mg). The solution is then evaporated to dryness under vacuum whilst swirling it around the sides of the containing vessel to produce a film. Tris (tris is an abbreviation for 2-amino, 2-hydroxymethylpropane 1, 3-diol) buffer (10 ml; 20 mM tris, 10 mM NaCl, pH 7.4) containing the active ingredient is added to the lipid when microvesicle formation occurs spontaneously.

The dispersion is shaken for 10 minutes to provide a crude distribution of vesicle sizes and the preparation is then sonicated under nitrogen at 2° C. in 5 ml portions using a probe sonicator for 5–10 minutes (1) in order to produce a bulk of liposomes of fairly small multi-laminar structure with 4 to 5 shells. (1) Sonication for 30 minutes gives unilamellar microvesicles and other variations may be used to produce liposomes of a different size than 4 to 5 shells. Reference should be made to other modifications which may be made in the procedure as described under Example 3.

Polymers (1) The polyvinyl stearate used in the microvesicle preparation described above is obtained as follows. Vinyl stearate (5 g) is added to toluene (7.5 ml) and the solution is stirred under nitrogen for 10 minutes. A solution of benzoyl peroxide (20 mg) in toluene (10 ml) is added and the mixture is refluxed for 2 hours. A further similar portion of benzoyl peroxide solution is then added and refluxing is continued for a further 16 hours. The toluene is removed by rotary evaporation and the resulting solid is purified by solution in chloroform and precipitation with methanol. The molecular weight of the polymer thus produced is typically about 7,000.

The vinyl stearate may be replaced by various vinyl alkanoates in order to provide polyvinyl alkanoates which are used in the microvesicle preparation in an analogous manner to the polyvinyl-stearate.

(2) In one variation of the microvesicle preparation procedure described above, the polyvinyl stearate is replaced with a copolymer of lauryl methacrylate and vinyl pyrrolidone prepared as follows. Lauryl methacrylate (14 g) and vinyl pyrrolidone (6 ml) are added to toluene (20 ml) and the solution is stirred under nitrogen at 100° C. whilst a solution of benzoyl peroxide (40 mg) in toluene (20 ml) is added. The mixture is heated under reflux for 2 hours before a further similar portion of benzoyl peroxide solution is added. The reaction mixture is heated under reflux and stirred overnight and the toluene is then removed by rotary evaporation, traces of monomer being removed by precipitation of the polymer in methanol from chloroform. The ratio of components in the polymer as derived from lauryl methacrylate:vinyl pyrrolidone is typically 4:1 by n.m.r. spectroscopy and the molecular weight is typically 9,500.

Further similar variations involve the use of copolymers of vinyl pyrrolidone with other alkyl methacrylates.

(3) In a second variation of the microvesicle preparation procedure described above, the polyvinyl stearate is replaced with a copolymer of vinyl alcohol and vinyl palmitate prepared as follows:

10 g of palmitic acid is dissolved in 100 ml of dimethylformamide (dried over 4 A molecular sieves) and thionyl chloride (2.55 ml) is added with stirring. The mixture is stirred for one hour at a temperature of 50°–55° C. and 1.05 g of polyvinylalcohol (molecular weight 3000, previously ground to facilitate easier dissolution) dissolved in 75 ml of hot dimethylformamide is added to the reaction mixture. The mixture of acid chloride and polymer in dimethylformamide is then stirred for three hours at 50° C. The resulting precipitate is separated by filtration, washed with distilled water and recrystallised from methanol. Characterisation of the resultant polymer by N.M.R. typically reveals a degree of esterification of 40%.

(4) In a third variation of the microvesicle preparation procedure described above, the polyvinyl stearate is replaced with polystearyl methacrylate prepared as follows:

Stearyl methacrylate (16.6 g) and benzoyl peroxide (0.83 g, 5% of monomer mass) are dissolved in 50 ml of toluene under nitrogen and the solution refluxed for 3 hours. The solvent is then removed by rotary evaporation and the polymer is dissolved in 25 ml chloroform. This solution is slowly poured into 800 ml of stirred methanol to produce precipitation of the polymer. The precipitate is consolidated by centrifugation and the supernatant carefully decanted off. The purified polymer is finally washed into a round bottomed flask with chloroform and rotary evaporation at 100° C. for 30 minutes is used to remove solvent. The molecular weight of the polymer thus produced is typically 10,000.

EXAMPLE 2

Variation in microvesicle half life in relation to polymer incorporation

Liposomes of 4–5 shells for the bulk of the population are prepared as described in Example 1 but varying the nature of the polymer added as shown in Table 1 and employing tris buffer containing no active ingredient. The various preparations are divided into a number of sealed individual samples for storage and subsequent tests.

The stability of the liposomes at 0° C. under nitrogen is followed in each instance by virtue of the ability of free liposomes at a temperature above the lipid phase transition temperature to undergo an osmotic response when placed in a hypertonic solution. The lipid phase transition temperature varies with lipid composition. Liposomes which have fused and/or which have formed lipid aggregates are not closed concentric structures and therefore do not show such an osmotic response. Shrinkage is produced by means of a hypertonic solution consisting of 100 mM leucine in the same tris buffer as is used in the preparation of the liposomes. Individual samples of the liposome preparations are removed from storage at intervals and the sample and the hypertonic solution are each pre-incubated at 37° C. and are then mixed in equal amounts in a cuvette which is maintained at 37° C. On mixing, the liposomes show an initial rapid shrinkage due to the expulsion of water in response to the large osmotic gradient. Subsequently, the still existing leucine gradient causes leucine and associated water to diffuse into the liposomes causing them to reswell. This diffusion process is followed by monitoring the light scattering of the mixture at 450 nm (Bangham et al, Chemistry and Physics of Lipids, 1967, 1, 225) and plotting the variation in the level of this scattering on a flat bed recorder with respect to time. The amplitude of the scattering is a measure of the population of intact liposomes so that its decrease with time provides a measure of the life of the liposomes.

Results typical of those obtained are shown in Table 1. A comparison of the lives of the various liposome preparations is provided by the half life ($T^{\frac{1}{2}}$) figure, this being the time taken for the population of liposomes to be reduced by 50%. It should be noted, however, that in general the population of liposomes decays away more quickly in the use of the control from this 50% point and that the $T^{\frac{1}{2}}$ figure is in many cases significantly better for the polymer-incorporating liposomes as compared with the control than is the $T^{\frac{1}{2}}$ figure.

Polymers

The 7,000 molecular weight polymer is prepared as described in Example 1 whilst the polymers of higher molecular weight are prepared by reducing the amount of initiator (for m.w. 17,500) and additionally by increasing the reflux period (for m.w. 100,000).

EXAMPLE 3

Variation in microvesicle half life in relation to polymer incorporation

In this series of experiments a wider range of polymers is studied than in Example 2 in order to compare the effect of variation in size of the lipophilic group at various polymer molecular weights and concentrations.

Liposomes of 4–5 shells for the bulk of the preparation are prepared using ovo-lecithin [1] as described in Example 1, but varying the nature and amount of the polymer added as shown in Table 2 and employing tris buffer containing no active ingredient. A modification as compared with the procedure of Example 4 is that throughout the preparation of the ovo-lecithin by the method of Dawson the solutions used are saturated with nitrogen and all stages of the microvesicle preparation are also carried out under an atmosphere of nitrogen.

The stability of the liposomes at 0° C. under nitrogen is followed by the procedure described in Example 2 which involves the monitoring of light scattering following osmotic shock treatment but in this case a temperature of 30° C. rather than 37° C. is employed for this treatment.

Results typical of those obtained are shown in Table 2. (1) In a variant of this procedure either phosphatidic acid or stearylamine is incorporated in the chloroform solution with the ovo-lecithin in an amount of 1 part by weight to nine parts by weight of the ovo-lecithin to give liposomes having a negative or positive surface charge, respectively. Stabilisation is again effected as compared with liposomes containing no polymer. Thus, in the case of the negatively charged liposomes, for example, typically $T^{\frac{1}{2}}$ for the control liposomes is about 50 days whilst none of the preparations of negatively charged liposomes corresponding to the preparations of neutral liposomes listed in Table 2 shows any appreciable change after 50 days.

Polymers

The polyvinyl alkanoate polymers used in the liposome preparations of this Example are prepared by one of the following modifications of the procedure described in relation to Example 1. (1) 15 g of vinyl alkanoate is dissolved in 50 ml dry toluene in a 100 ml round bottomed flask and 0.75 g (5% w/w of monomer)

of benzoyl peroxide in 15 ml toluene is added. Antibumping granules are added, the reaction mixture is purged with $N_2$ for 10 minutes and then slowly brought up to reflux temperature. After a two hour reflux, solvent is removed by rotary evaporation and the polymer dissolved in 25 ml chloroform. This solution is slowly poured into 800 ml of stirred methanol to effect precipitation of the polymer. The precipitate is consolidated by centrifugation and the supernatant carefully decanted off. The purified polymer is finally washed into a round bottomed flask with chloroform and rotary evaporation at 100° C. for 30 minutes is used to remove solvent.

Using the amount of benzoyl peroxide indicated above (5% w/w of monomer), polyvinyl alkanoates with a molecular weight in the range of 7,000 to 10,000 are typically obtained. By decreasing the proportion of initiator to 0.05% w/w of monomer the molecular weight is increased, typically in the range of 15,000 to 20,000, whilst the use of intermediate amounts of initiator gives polymers of molecular weight lying between these two ranges. (2) 50 ml of an initiator solution of azobisisobutyronitrile in benzene (2 mg/ml) is added to 15 g of vinyl stearate in a 100 ml round-bottomed flask together with a further 20 ml benzene. Antibumping granules are added and the solution purged with $N_2$ for 10 minutes. After refluxing for 1 hour a further 5 ml of the initiator solution (stored in a fridge following its making up just prior to commencement of the preparation) is added and refluxing continued for 3 more hours. The solvent is then removed by rotary evaporation and the resulting polymer is dissolved in 25 ml $CHCl_3$. This solution is poured slowly into 800 ml of stirred methanol which causes precipitation of the purified polymer. The precipitate is consolidated by centrifugation and the supernatant is carefully decanted off. The polymer is finally washed into a round bottomed flask with chloroform and solvent is then removed by rotary evaporation at 100° C. for 30 minutes. The molecular weight of the polymer produced by this procedure is typically 25,000. Use of 25 ml of a 2 mg/ml initiator solution typically gives a polymer of molecular weight 35,000 whilst the use of intermediate amounts of initiator gives polymers of molecular weight intermediate between 25,000 and 35,000.

EXAMPLE 4

Immunogenicity of polymer-containing unilamellar virosome preparations

Liposomes of 4-5 shells for the bulk of the population and containing polyvinyl stearate (m.w7,000) or the lauryl methacrylate/vinyl pyrrolidone copolymer are prepared as described in Example 1 but omitting any active ingredient from the tris buffer. 0.1 ml of each liposome preparation is then treated with an equal volume of X31 influenza virus polymer subunits in tris buffer (20 mM tris, 10 mM NaCl, pH 7.4) at 1 mg/ml. The mixture is sonicated in a cold water bath for 15 minutes to form unilamellar virosomes and then kept at 4° C. until used. As one form of control, unilamellar-virosomes are prepared as just described but omitting any polymer.

Virosomes containing each polymer, virosomes containing no polymer and subunits alone are each injected intraperitoneally at 10 μg and 50 μg dosage levels into separate groups of five mice, a further group of five uninoculated mice acting as controls. Two weeks later, the antibody levels produced by the injections are compared by assaying the amount of Haemaglutination Inhibition (HI) produced in each case, typical results being shown in Table 3. Although variations occur according to polymer used, dose levels, etc., it will be seen that the incorporation of the polymer into the virosomes does in no case seriously inhibit the serological response and in some cases actually potentiates it.

Polymer-containing virosomes prepared according to this Example show no settling out during storage over a considerable period, in contrast to preparations lacking the polymers which show settling out within a few days or a week.

EXAMPLE 5

Polymer-containing virosomes formed with different lipids

Liposomes of 4–5 shells for the bulk of the population are prepared as described in Example 1 and containing polyvinly stearate m.w.7,000) but omitting any active ingredient from the tris buffer and, in addition to the use of ovo lecithin in one preparation using instead the same amount of either dipalmitoyl phosphatidylcholine or sphingomyelin in two further preparations.

Unilamellar virosomes are then prepared in the case of each of the three preparations by the use of the procedure described in Example 4. The immunogenicity of each virosome preparation and of X31 influenza virus polymer subunits is measured in a similar manner to that described in Example 4, typical results being shown in Table 4. It will be seen that in general the virosomes show an adjuvant immunogenic enhancement of the response of the influenza virus subunits. The sphingomyelin based virosomes show somewhat inconsistent results between the two dosage levels but this is probably due to the unusual gelatinous condition of these preparations which could have a more marked effect on immunogenic potency in the case of the smaller amount of subunit material present at the lower dosage level.

Polymer-containing virosomes prepared according to this Example show no settling out during storage over a considerable period, in contrast to preparations lacking the polymer which show settling out within a few days or a week.

EXAMPLE 6

Polymer stabilised liposomes containing cortisol palmitate (All operations are carried out under nitrogen)

Ovo-lecithin (8.5 mg), phosphatidic acid (0.85 mg), [$^3$H] cortisol palmitate (0.5 mg, 0.13μCi) and polyvinyl stearate (93.5μg; m.w. 7,000—prepared as described in Example 3) are mixed in chloroform (0.1 ml) and the chloroform then removed from the solution by rotary evaporation. Tris buffer (2 ml; 20 mM tris, 10 mM NaCl, pH 7.4) is then added to the residual mixture from the evaporation and the resulting liposome suspension is shaken for 1 hour.

The liposomes thus formed are centrifuged at 50,000 g for 20 minutes at 5° C. and then washed by resuspending in fresh buffer, centrifuging, and resuspending again in 1 ml of fresh buffer. The liposome suspension (1 ml) is diluted by the addition of tris buffer (9 ml).

A control experiment is carried out using the procedure described above but omitting the polyvinyl stearate.

The level of [$^3$H] cortisol palmitate retention in both the polyvinly stearate containing and the control liposomes is studied using the method of Shaw et al, Biochemical Journal, 1976, 158, 473–6. From the liposome suspension a 0.1 ml sample is taken for scintillation counting and at 24 hour intervals thereafter the liposomes are centrifuged for 20 minutes at 50,000 g, resuspended in the same volume of buffer and a further 0.1 ml sample taken for counting.

The results obtained for [$^3$H] cortisol palmitate retention are similar to those reported by Shaw et al and, typically, no difference in retention of [$^3$H] cortisol phosphate is seen between the polyvinyl stearate containing liposomes and the control liposomes.

Comparison of the stability of the two liposome preparations by the procedure described in Example 2 typically shows a similar level of stabilisation for the polyvinyl stearate containing liposomes over the controls as is shown in Table 2.

EXAMPLE 7

Polymer stabilised liposomes containing insulin

Insulin (1 mg) is dissolved in tris buffer (1 ml, 20 mM tris, 10 mM NaCl) together with chloramine T (1 mg). To the solution is added Na[$^{125}$I] (10 μCi) and after incubation for 1 minute 0.1 ml of a solution of sodium metabisulphite in tris buffer (24 mg/ml) is added. The mixture is then passed down a Sephadex G10 column (0.5 cm×7 cm) eluting with tris buffer to separate the [$^{125}$I]-labelled insulin from the free [$^{125}$I].

The [$^{125}$I] insulin is added in 2 ml of tris buffer to ovolecithin (40 mg) and polyvinyl stearate (0.4 mg, m.w. 7,000 prepared as described under Example 3). The suspension is hand shaken, then sonicated for 5 minutes. The resulting liposome suspension (1 ml) is passed down a Sephadex G-50 column (2 cm×32 cm) eluting with tris buffer to separate any free [$^{125}$I] labelled insulin from the liposomes. The liposome fraction is collected and stored at 2° C.

Samples of the liposome preparation are passed down a Sephadex G-50 column (2 cm×32 cm) eluting with tris buffer to assess loss of [$^{125}$I]-insulin after 1 and 4 days. It is typically found that only a small amount of the insulin is lost over this time period.

Comparison of the stability of the two liposome preparations by the procedure described in Example 2 typically shows a similar level of stabilisation for the polyvinyl stearate containing liposomes over the controls as is shown in Table 2.

TABLE 1

Variation in microvesicle half life in relation to polymer incorporation

| Polymer[1] | Molecular Weight | Concentration lecithin:polymer (w/w) | T½ days |
|---|---|---|---|
| Polyvinyl Stearate | 7,000 | 100:1 | 40 |
| Polyvinyl Stearate | 17,500 | 100:1 | 20 |
| Polyvinyl Stearate | 100,000 | 100:1 | 24 |
| Polyvinyl Stearate | 7,000 | 4:1 | 60 |
| Polyvinyl Stearate | 7,000 | 75:1 | 50 |
| Polyvinyl Stearate | 7,000 | 15:1 | 40 |
| Polyvinyl Stearate | 7,000 | 100:1 | 50 |
| Polyvinyl Stearate | 7,000 | 150:1 | 100 |
| Polyvinyl Stearate | 7,000 | 500:1 | (2) |
| Polyvinyl Stearate | 7,000 | 4:1 | 60 |
| Vinyl Stearate | — | 4:1 | 40[3] |
| U.V. Irradiated Vinyl Stearate | — | 4:1 | 110 |
| Ethyl Stearate | — | 4:1 | 10 |

[1]Liposomes from which the 10mg of polyvinyl stearate is omitted without any replacement show a half life of 16 days (±5 days S.D. over 9 determinants).
[2]After an initial fall in the amplitude of light scattering at 450mm over the first 7 days, the amplitude remains constant for the remainder of the experiment (Total 35 days).
[3]Increase in half life believed to be due to the occurrence of spontaneous polymerisation.

TABLE 2

Variation in microvesicle half life in relation to polymer incorporation

| Polyvinyl alcohol ester[1] C atoms in lipophilic groups | Molecular weight | Concentration polymer:lecithin (% by weight) | T½ days |
|---|---|---|---|
| $C_8$ | 9,000 | 1 | 48 |
| $C_8$ | 9,000 | 5 | 64 |
| $C_{10}$ | 7,000 | 5 | 48 |
| $C_{12}$ | 11,500 | 0.5 | 39 |
| $C_{12}$ | 11,500 | 1 | 42 |
| $C_{12}$ | 11,500 | 5 | 56 |
| $C_{14}$ | 7,000 | 1 | 70 |
| $C_{14}$ | 24,000 | 1 | 160 |
| $C_{16}$ | 7,000 | 1 | 200 |
| $C_{16}$ | 16,000 | 1 | 86 |
| $C_{18}$ | 7,000 | 0.5 | 96 |
| $C_{18}$ | 7,000 | 1 | 48 |
| $C_{18}$ | 7,000 | 5 | (2) |
| $C_{18}$ | 19,000 | 0.5 | 60 |
| $C_{18}$ | 19,000 | 1 | 69 |
| $C_{18}$ | 19,000 | 5 | 56 |
| $C_{24}$ | 7,000 | 1 | 41 |

[1]Liposomes containing no polymer show a half life of 18 (± 7 days SD)
[2]These liposomes were unstable towards osmotic shock.

TABLE 3

Immunogenicity of polymer-containing virosome preparations.

| | | HI Response | | | |
|---|---|---|---|---|---|
| Antigen[1] | Mouse | Dose 10 μg Individual | Dose 10 μg Group Mean | Dose 50 μg Individual | Dose 50 μg Group Mean |
| Virosomes without polymer | 1 | 18 | 13.64 | 18 | 21.9 |
| | 2 | 9 | | 36 | |
| | 3 | 18 | | 24 | |
| | 4 | 18 | | 36 | |
| | 5 | 9 | | 9 | |
| Virosomes containing Polyvinyl stearate | 1 | 9 | 4.65 | 36 | 25.15 |
| | 2 | <6 | | 36 | |
| | 3 | <6 | | 36 | |
| | 4 | 9 | | 18 | |
| | 5 | <6 | | 12 | |
| Virosomes containing Lauryl methacrylate-vinyl pyrrolidone polymer | 1 | 9 | 8.79 | 36 | 29.89 |
| | 2 | 9 | | 48 | |
| | 3 | 24 | | 24 | |
| | 4 | 9 | | 24 | |
| | 5 | <6 | | 24 | |
| Subunits only | 1 | <6 | 5.34 | 36 | 20.19 |
| | 2 | <6 | | 24 | |
| | 3 | 9 | | 9 | |
| | 4 | 18 | | 24 | |
| | 5 | <6 | | 18 | |
| Inoculated | 1 | <6 | <6 | | |
| | 2 | <6 | | | |
| | 3 | <6 | | | |
| | 4 | <6 | | | |
| | 5 | <6 | | | |

[1]Control antigen titration = 12 HAU

TABLE 4

Polymer-containing virosomes formed with different lipids

| Antigen[1] | Mouse | HI Response Dose Individual (10 μg) | 10 μg Group Mean | Dose Individual (50 μg) | 50 μg Group Mean |
|---|---|---|---|---|---|
| Ovo lecithin virosomes | 1 | 48 | 26.02 | 48 | 24.5 |
|  | 2 | 18 |  | 18 |  |
|  | 3 | 24 |  | 18 |  |
|  | 4 | 24 |  | 24 |  |
|  | 5 | 24 |  | 24 |  |
| Dipalmitoyl phosphatidyl choline virosomes | 1 | 18 | 20.67 | 9 | 28.89 |
|  | 2 | 18 |  | 36 |  |
|  | 3 | 18 |  | 36 |  |
|  | 4 | 18 |  | 48 |  |
|  | 5 | 36 |  | 36 |  |
| Sphingomyelin virosomes | 1 | 9 | 5.34 | 48 | 44.66 |
|  | 2 | <6 |  | 36 |  |
|  | 3 | <6 |  | 128 |  |
|  | 4 | 9 |  | 18 |  |
|  | 5 | 6 |  | 36 |  |
| Subunits alone | 1 | <6 | 4.29 | 36 | 20.19 |
|  | 2 | <6 |  | 9 |  |
|  | 3 | <6 |  | 36 |  |
|  | 4 | <6 |  | 12 |  |
|  | 5 | 18 |  | 24 |  |
| Uninoculated | 1 | <6 | <6 |  |  |
|  | 2 | <6 |  |  |  |
|  | 3 | <6 |  |  |  |
|  | 4 | <6 |  |  |  |
|  | 5 | <6 |  |  |  |

[1]Control antigen titration = 12 HAU

We claim:

1. Liposomes incorporating a polymer having aliphatic lipophilic groups with a chain of at least six atoms attached to the backbone thereof and having a molecular weight of from 2,000 to 50,000 wherein the proportion of polymer to the lipid content of the liposomes is in a range from 1 part by weight of the polymer to from 10 to 1,000 parts by weight of the lipid.

2. Liposomes according to claim 1, wherein the lipophilic groups have a chain of at least twelve atoms.

3. Liposomes according to claim 1, wherein the lipophilic groups have a chain of up to and including thirty atoms.

4. Liposomes according to claim 1 wherein the lipophilic groups comprise a chain of carbon atoms and the residue of a functional grouping through which this is attached to the polymer backbone.

5. Liposomes according to claim 4, wherein the chain of carbon atoms is the residue of a straight chain hydrocarbon.

6. Liposomes according to claim 5, wherein the chain of carbon atoms is a n-tridecyl, n-tetradecyl, n-pentadecyl, n-hexadecyl, n-heptadecyl, n-octadecyl, oleyl, or n-nonadecyl group.

7. Liposomes according to claim 4 wherein the functional residue is an oxycarbonyl group.

8. Liposomes according to claim 1, wherein the polymer backbone comprises a chain of carbon atoms.

9. Liposomes according to claim 1, wherein the polymer is a derivative of polyvinyl alcohol, polyacrylic acid or polymethacrylic acid.

10. Liposomes according to claim 9, wherein the polymer is an ester derivative, being a polyvinyl alcohol ester, a polyacrylate or a polymethacrylate.

11. Liposomes according to claim 10, wherein the polymer is n-tetradecyl- polyacrylate or polymethacrylate, n-hexadecyl- polyacrylate or polymethacrylate, n-octadecyl- polyacrylate or polymethacrylate, polyvinyl myristate, polyvinyl palmitate, or polyvinyl stearate.

12. Liposomes according to claim 1, wherein the proportion of polymer to the lipid content of the microvesicles is in a range from 1 part by weight of the polymer to from 20 to 200 parts by weight of the lipid.

13. Liposomes according to claim 1, wherein the lipid content of the liposomes is substantially comprised of lipids having aliphatic chains of from fourteen to eighteen carbon atoms.

14. Liposomes according to claim 1, wherein the polymer has a molecular weight of from 5,000 to 40,000.

15. A composition comprising liposomes according to claim 1 incorporating a physiologically active substance.

16. A composition according to claim 15, wherein the physiologically active substance is an antigenic material.

17. A composition according to claim 15, wherein the physiologically active substance is an anti-inflammatory agent.

18. A composition according to claim 15, wherein the physiologically active substance is a hormone.

19. A composition according to claim 15, wherein the liposomes carry a neutral or negative surface charge.

20. A method for the treatment of a human or other mammalian patient with a physiologically active substance which comprises administering said substance to the patient incorporated with liposomes according to claim 1.

* * * * *